United States Patent
Gal et al.

(10) Patent No.: US 8,235,897 B2
(45) Date of Patent: Aug. 7, 2012

(54) DEVICE FOR NON-INVASIVELY MEASURING GLUCOSE

(75) Inventors: Avner Gal, Hertzeliya (IL); Alexander M. Raykhman, East Greenwich, RI (US); Eugene Naidis, Ashkelon (IL); Yulia Mayzel, Beer-Sheva (IL); Alexander Klionsky, Ashdod (IL); Anatoly Diber, Ashkelon (IL)

(73) Assignee: A.D. Integrity Applications Ltd., Ashkelon (IL)

( * ) Notice: Subject to any disclaimer, the term of this patent is extended or adjusted under 35 U.S.C. 154(b) by 0 days.

(21) Appl. No.: 13/090,535

(22) Filed: Apr. 20, 2011

(65) Prior Publication Data

US 2011/0263956 A1    Oct. 27, 2011

Related U.S. Application Data

(60) Provisional application No. 61/328,344, filed on Apr. 27, 2010.

(51) Int. Cl.
*A61B 5/00* (2006.01)
(52) U.S. Cl. .......................................... 600/365; 600/309
(58) Field of Classification Search .................. 600/300, 600/347, 365
See application file for complete search history.

(56) References Cited

U.S. PATENT DOCUMENTS

| | | |
|---|---|---|
| 3,085,566 A | 4/1963 | Tolles et al. |
| 3,412,729 A | 11/1968 | Smith, Jr. |
| 3,638,640 A | 2/1972 | Shaw |
| 4,859,078 A | 8/1989 | Bowman |
| 5,070,874 A | 12/1991 | Barnes |
| 5,086,229 A | 2/1992 | Rosenthal |
| 5,119,819 A | 6/1992 | Thomas et al. |
| 5,361,758 A | 11/1994 | Hall |
| 5,395,033 A * | 3/1995 | Byrne et al. .............. 227/175.1 |
| 5,657,754 A | 8/1997 | Rosencwaig |

(Continued)

FOREIGN PATENT DOCUMENTS

EP    1774902    4/2007

(Continued)

OTHER PUBLICATIONS

Noninvasive glucose Determination by Oscillating Thermal Gradient Spectrometry; P Zheng, CE Kramer, CW Barnes, JR Braig, BB Sterling; Diabetes Technology & Therapeutics, vol. 2, No. 1, 2000.*

(Continued)

*Primary Examiner* — Navin Natnithithadha
*Assistant Examiner* — Karen Toth
(74) *Attorney, Agent, or Firm* — Wiggin and Dana LLP; Gregory S. Rosenblatt

(57) ABSTRACT

In order to increase the accuracy of non-invasive glucose measurement, the device uses a combination of three non-invasive methods: ultrasonic, electromagnetic and thermal. The non-invasive glucose monitor comprises a Main Unit, which drives three different sensor channels (one per technology), located on an external unit configured as an ear clip attached to the subject's ear lobe. To effect the ultrasonic channel, ultrasonic piezo elements are positioned on opposing portions of the ear clip and thus opposite sides of the ear lobe. For implementation of the electromagnetic channel, capacitor plates are positioned on opposing portions of the ear clip and the ear lobe serves as the dielectric. The thermal channel includes a heater and a sensor positioned on the ear clip in close juxtaposition to the ear lobe.

8 Claims, 10 Drawing Sheets

U.S. PATENT DOCUMENTS

| | | | |
|---|---|---|---|
| 5,666,956 A | 9/1997 | Buchert | |
| 5,676,143 A | 10/1997 | Simonsen | |
| 5,687,721 A | 11/1997 | Kuhls | |
| 5,747,672 A | 5/1998 | Parent et al. | |
| 5,752,512 A | 5/1998 | Gazani | |
| 5,771,891 A | 6/1998 | Gozani | |
| 5,788,632 A | 8/1998 | Pezzaniti | |
| 5,792,668 A | 8/1998 | Fuller | |
| 5,795,305 A * | 8/1998 | Cho et al. | 600/549 |
| 5,910,109 A | 6/1999 | Peters | |
| 5,924,996 A * | 7/1999 | Cho et al. | 600/549 |
| 5,941,821 A | 8/1999 | Cho | |
| 5,944,179 A | 8/1999 | Walker | |
| 6,044,285 A | 3/2000 | Chaiken | |
| 6,049,728 A | 4/2000 | Chou | |
| 6,070,093 A | 5/2000 | Oosta | |
| 6,289,230 B1 | 9/2001 | Chaiken | |
| 6,362,144 B1 | 3/2002 | Berman | |
| 6,377,828 B1 | 4/2002 | Chaiken | |
| 6,405,069 B1 * | 6/2002 | Oraevsky et al. | 600/407 |
| 6,517,482 B1 * | 2/2003 | Elden et al. | 600/309 |
| 6,636,753 B1 | 10/2003 | Braig | |
| 6,749,740 B2 | 6/2004 | Liamos | |
| 6,882,940 B2 | 4/2005 | Potts | |
| 6,887,239 B2 | 5/2005 | Elstrom | |
| 6,944,486 B2 | 9/2005 | Braig | |
| 6,949,070 B2 | 9/2005 | Ishler | |
| 6,999,810 B2 | 2/2006 | Berner | |
| 7,003,336 B2 | 2/2006 | Holker | |
| 7,011,630 B2 | 3/2006 | Desai | |
| 7,020,506 B2 | 3/2006 | Fine | |
| 7,022,071 B2 | 4/2006 | Schaupp | |
| 7,029,444 B2 | 4/2006 | Shin | |
| 7,050,847 B2 | 5/2006 | Ollmar | |
| 7,058,437 B2 | 6/2006 | Buse | |
| 7,074,307 B2 | 7/2006 | Simpson | |
| 7,079,881 B2 | 7/2006 | Schulman | |
| 7,087,017 B2 | 8/2006 | Christopherson | |
| 7,120,483 B2 | 10/2006 | Russell | |
| 7,254,426 B2 | 8/2007 | Cho et al. | |
| 7,666,151 B2 * | 2/2010 | Sullivan et al. | 600/587 |
| 2003/0013947 A1 | 1/2003 | Frattarola | |
| 2005/0043602 A1 | 2/2005 | Freger | |
| 2006/0175205 A1 | 8/2006 | Cui | |
| 2007/0132043 A1 | 6/2007 | Bradley et al. | |
| 2009/0105605 A1 * | 4/2009 | Abreu | 600/549 |
| 2010/0007330 A1 * | 1/2010 | Shih et al. | 324/76.77 |
| 2010/0010323 A1 | 1/2010 | Jobst | |
| 2010/0030045 A1 | 2/2010 | Gottlieb | |
| 2010/0049007 A1 * | 2/2010 | Sterling et al. | 600/301 |
| 2010/0298667 A1 * | 11/2010 | Uenishi et al. | 600/301 |

FOREIGN PATENT DOCUMENTS

| | | |
|---|---|---|
| EP | 1818910 | 8/2007 |
| GB | 2422197 | 7/2006 |
| JP | 03010101 | 1/1991 |
| WO | WO0053085 | 9/2000 |
| WO | WO2004106889 | 12/2004 |
| WO | WO2005018443 | 3/2005 |
| WO | WO2005073393 | 8/2005 |
| WO | WO2006096080 | 9/2006 |
| WO | WO2007130694 | 11/2007 |

OTHER PUBLICATIONS

Monitoring Blood Glucose Changes in Cutaneous Tissue by Temperature-modulated Localized Reflectance Measurements, Sju-Jen Yeh, Charles F. Hanna, Omar S. Khalil; Clinical Chemistry, 49:6, 924-934 (2003).*

First human experiments with a novel non-invasive, non-optical continuous glucose monitoring system, A Caduff, E Hirt, Y Feldman, Z Ali, L Heinemann; Biosensors and Bioelectronics 19 (2003) 209-217.*

A Novel Noninvasive Blood Glucose Monitor, CD Malchoff, K Schukri, JI Landau, JM Buchert; Diabetes Care, vol. 25, No. 12, Dec. 2002.*

PCT/IL 11/00328 International Search Report mailed Oct. 12, 2011, 13 pages.

Journal of Diabetes Science and Technology, vol. 3, Issue 2, Mar. 2009, "Noninvasive Glucose Monitoring: A Novel Approach"; Harman-Boehm, M.D., et al., pp. 253-260, p. 255, col. 2, para. 1; p. 256, col. 2, para. 3; Fig. 2, 3.

* cited by examiner

DEVICE FOR NON-INVASIVELY MEASURING GLUCOSE

CROSS REFERENCE TO RELATED APPLICATIONS

This application is based on and claims domestic priority benefits under 35 U.S.C. 120 of U.S. Provisional patent application 61/328,344, filed 27 Apr. 2010. The entire Provisional application is hereby incorporated by reference herein.

FIELD OF THE INVENTION

This invention relates to the medical field and the treatment of specified diseases and, in particular, to a device for non-invasive measurement of the blood glucose level of a subject patient.

BACKGROUND OF THE INVENTION

Diabetes and its complications impose significant economic consequences on individuals, families, health systems and countries. The annual expenditure for diabetes in 2007 in the USA alone was estimated to be over $170 billion, attributed to both direct and indirect costs (American Diabetes Association. Economic costs of diabetes in the U.S. in 2007. *Diabetes Care.* 2008 March, 31(3): 1-20). In 2010, Healthcare expenditures on diabetes are expected to account for 11.6% of the total worldwide healthcare expenditure. It is estimated that approximately 285 million people around the globe will have diabetes in 2010, representing 6.6% of the world's adult population, with a prediction for 438 million by 2030 (International Diabetes Federation. Diabetes Atlas, Fourth edition. International Diabetes Federation, 2009).

In the recent years, research has conclusively shown that improved glucose control reduces the long-term complications of diabetes (DCCT Research Group. The effect of intensive treatment of diabetes on the development and progression of long-term complications in insulin-dependent diabetes mellitus. *North England Journal of Medicine.* 1993 Sep. 30; 329(14): 977-986; UKPDS Group: Intensive blood-glucose control with sulphonylureas or insulin compared with conventional treatment and risk of complications in subjects with type 2 diabetes (UKPDS33). *The Lancet.* 1998 Sep. 12; 352(9131): 837-853). According to the American Diabetes Association (ADA), self-monitoring of blood glucose (SMBG) has a positive impact on the outcome of therapy with insulin, oral agents and medical nutrition (American Diabetes Association. Clinical Practice Recommendations, Standards of medical care in diabetes. *Diabetes Care.* 2006 Jan 29: S4-S42). In its publication "Consensus Statement: A European Perspective", the Diabetes Research Institute in Munich recommends SMBG for all types of diabetes treatment approaches, in order to achieve proper glucose control and values which are close to normal, without increasing the risk of hypoglycemia (Schnell O et al., *Diabetes*, Stoffwechsel and Herz, 2009; 4:285-289). Furthermore, special guidelines with proper recommendations were issued recently by the International Diabetes Federation (IDF), to support SMBG for non-insulin treated T2DM patients (Recommendations based on a workshop of the International Diabetes Federation Clinical Guidelines Taskforce in collaboration with the SMBG International Working group. Guidelines on Self-Monitoring of Blood Glucose in Non-Insulin Treated Type 2 Diabetics. International Diabetes Federation, 2009).

SMBG presents several benefits in both diabetes education and treatment. It can help facilitate individuals' diabetes management by providing an instrument for objective feedback on the impact of daily lifestyle habits, individual glucose profiles, including exercise and food intake impact on that profile, and thereby empower the individual to make necessary changes. Moreover, SMBG can support the healthcare team in providing individually tailored advice about life style components and blood glucose (BG) lowering medications, thus helping to achieve specific glycemic goals.

The inconvenience, expenses, pain and complexity involved in conventional (invasive) SMBG, however, lead to its underutilization, mainly in people with type 2 diabetes (Mollema E D, Snoek F J, Heine R J, Van der Ploeg H M. Phobia of self-injecting and self-testing in insulin treated diabetes patients: Opportunities for screening. *Diabet Med.* 2001; 18:671-674; Davidson M B, Castellanos M, Kain D, Duran P. The effect of self monitoring of blood glucose concentrations on glycated hemoglobin levels in diabetic patients not taking insulin: a blinded, randomized trial. *Am J Med.* 2005; 118(4):422-425; Hall R F, Joseph D H, Schwartz-Barcott D: Overcoming obstacles to behavior change in diabetes self-management. *Diabetes Educ.* 2003; 29:303-311). Availability of an accurate, painless, inexpensive and easy to operate device will encourage more frequent testing (Wagner J, Malchoff C, Abbott G. Invasiveness as a Barrier to Self-Monitoring of Blood Glucose in Diabetes. *Diabetes Technology & Therapeutics.* 2005 August; 7(4): 612-619; Soumerai S B, Mab C, Zhan F, Adams A, Baron M, Fajtova V, Ross-Degnan D. Effects of health maintenance organization coverage of self-monitoring devices on diabetes self-care and glycemic control. *Arch Intern Med.* 2004; 164:645-652), leading to tighter glucose control and delay/decrease of long-term complications and their associated healthcare costs.

Non-invasive (NI) glucose monitoring can decrease the cost of SMBG and increase meaningfully the frequency of testing. The main concern in NI methods is to achieve high accuracy results, despite the fact that no direct blood or interstitial fluid measurement is performed.

Therefore, as is well known in the medical arts, one of the more important blood components to measure for diagnostic purposes is glucose, especially for diabetic patients. The well-known and typical technique for determining blood glucose concentration is to secure a blood sample and apply that blood to an enzymatically medicated colorimetric strip or an electrochemical probe. Generally, this is accomplished from a finger prick. For diabetic patients who may need to measure blood glucose a few times a day, it can immediately be appreciated that this procedure causes a great deal of discomfort, considerable irritation to the skin and, particularly, the finger being pricked, and, of course, infection.

For many years, there have been a number of procedures for monitoring and measuring the glucose level in humans and animals. These methods, however, generally involve invasive techniques and, thus, have some degree of risk, or at least some discomfort, to the patient. Recently, some non-invasive procedures have been developed, but still they do not always provide optimum measurements of the blood glucose. At present, there has been no practical confirmed solution.

Most non-invasive monitoring techniques have focused on using incident radiation, which is capable of penetrating tissue and probing the blood. Currently known approaches to non-invasive glucose measurement are mainly based on optical technology. The less successful and relatively uncommon electrical measurements focus upon the dielectric properties of water solutions in a given frequency range, typically between 1-50 MHz. In one form or another, such methods attempt to monitor the influence of glucose or other analyzed concentration upon the dielectric frequency response of either the glucose itself or the secondary effect on the water.

Although investigations have been made into the use of acoustic monitoring, past studies have been primarily directed to the differences in acoustic velocity between organs. These studies have attempted to correlate acoustic velocity changes with chronic or continuous disease states. In addition, there is a large body of medical and scientific literature pertaining to the use of acoustic absorptive and scattering properties of organs for imaging, therapeutic and even diagnostic objectives.

In the prior art techniques, only one parameter is measured. Thus, the possibility of an error is increased.

Freger (U.S. Pat. No. 6,954,662) discloses a non-invasive technique and methods (but not devices) for measurements of the speed of sound through the blood, the conductivity of the blood, and the heat capacity of the blood. Thereafter, the glucose level for each of the three measurements is calculated and the final glucose value is determined by a weighted average of the three calculated glucose values.

While Freger mentions that measurements may be taken of the speed of sound through the blood, the conductivity of the blood, and the heat capacity of the blood, there is no disclosure of how any device can be constructed for effecting such measurements. The herein disclosed and claimed invention, therefore, is an improvement of Freger and specifies a specific device in which these measurements can be effected.

Therefore, there is a need for a more accurate non-invasive device for measuring glucose level, by means of monitoring multiple parameters in a single unitary device. It is, therefore, an object of the present invention to provide a device for non-invasively measuring glucose level in a subject. These objects are achieved by the features of the claims and the following description, in particular by the following preferred aspects of the invention relating to preferred additional and/or alternative embodiments.

SUMMARY OF THE INVENTION

This and other objects of the Invention are achieved by a device, preferably an unitary device, that is capable of non-invasively measuring the body's glucose level by three distinct protocols.

In particular, the device according to the present invention preferably includes a Main Unit, containing hardware and also the software applications, and preferably an external unit(s)/external device(s) (preferably an ear clip) for affixment to the patient. The external unit comprises first and second portions which are connected to each other, wherein the first and second portions are located on opposing sides of a part of the subject, to which said external unit is affixed. For instance, when the external unit is affixed to a patient's ear lobe, the two opposing sides are located on the two opposing sides of the ear lobe, respectively It is preferable to incorporate in the unitary external unit at least one of the following three elements, which effect three separate and distinct non-invasive measurements of glucose. Additionally, it is further preferred to provide at least two or three elements to effect two or three separate and distinct non-invasive measurements of glucose, respectively. According to a preferred embodiment of the present invention, at least three different elements to effect three separate and distinct non-invasive measurements of glucose are provided within a single, unitary external device, e.g., within a single housing.

It should also be appreciated and understood that each of the measurement channels is new and novel in and of themselves. Hence each measurement channel may be used in isolation by itself (or with still other measurement channels). By combining the three measurement channels in one unitary device, measurements are obtained from three separate and unique measurement channels, thereby optimizing the final measurement.

For non-invasive measurement by use of ultra sound, preferably a transmitter (such as an ultra sound transmitter) and a receiver (such as an ultrasound receiver) are mounted on opposing sides of the external unit. When the external unit is fitted on the patient, a portion of the patient's body (such as an ear lobe) is situated between the transmitter and receiver. Upon receipt of the resultant signal, after it passes through the patient, the receiver sends the signal to the Main Unit for processing by appropriate algorithms. In some embodiments, membranes may be used to cover and protect the transmitter and receiver.

To effect an Electromagnetic measurement, a capacitor is defined in the external unit. The capacitor plates are positioned on opposing sides of the external device and the body part (such as an ear lobe) disposed between the parts of the external unit serves as the dielectric. In some cases the membranes used to shield or cover the transmitter and receiver can serve also as the capacitor plates.

The third technology is based on thermal technology to measure the glucose level. For this purpose, preferably a heater and a sensor are provided at the external device. It is preferred to provide the heater and the sensor (thermal sensor) at opposing sides of the external device. According to another preferred embodiment, however, it is preferred to mount the heater and the sensor on the same side of the two opposing sides, e.g., on the tip of one side of the external unit a heater and sensor are positioned.

The objects of the present invention are solved, for example, by the following aspects of the invention.

According to a first aspect, a unitary device for non-invasively measuring glucose level in a subject comprises: ultrasonic piezo elements positioned on opposing portions of the device and surrounding a part of the subject's body to which the device is attachable; capacitor plates positioned on opposing portions of said device and surrounding said part of the subject's body to which the external means is attachable, and auto-oscillating means connected to said capacitor plates; and a heater and a sensor positioned in close juxtaposition to said part of the subject's body to which the device is attachable.

In one preferred embodiment, the device further comprises an external means (such as an ear clip) for affixment to the subject's body, wherein the ultrasonic piezo elements, the capacitor plates and the heater and the sensor being contained within said external means.

There may also preferably be a main unit for controlling measurements and calculating glucose level; and, means for electrically connecting the main unit and the external means, either galvanic or wireless.

Preferably, membranes cover the ultrasonic piezo elements.

The ultrasonic piezo elements may preferably include a transducer and a receiver.

Preferably, the capacitor plates comprise membranes. In such an embodiment, the membranes may also cover the ultrasonic piezo elements.

A preferred embodiment may include means for determining a distance between opposing portions of said external means. In some embodiments, this means may include a magnet and a sensor.

There may also preferably be an adjustment screw setting the distance between opposing portions of said external means.

In some embodiments, an ambient temperature sensor may be included.

According to other aspects, the individual measurements channels may be separately utilized.

According to a second aspect of the invention, a device for non-invasively measuring glucose level in a subject may comprise a housing; and, capacitor plates positioned on opposing portions of the housing and surrounding a part of the subject's body to which the device is attachable, and auto-oscillating means connected to the capacitor plates.

In a preferred embodiment, this device also includes a processing means for calculating glucose level based on a tissue impedance signal, and means for communicating the tissue impedance signal to the processing means.

This embodiment may include capacitor plates comprised of membranes.

According to an alternate version of this embodiment, there may also be ultrasonic piezo elements positioned on opposing portions of the housing and surrounding said part of the subject's body to which the device is attachable. It may include capacitor plates comprised of membranes and the membranes may cover the ultrasonic piezo elements.

A different alternate version of this embodiment, may include ultrasonic piezo elements positioned on opposing portions of the housing and surrounding the part of the subject's body to which the device is attachable, means for detecting a phase shift between a transmitted and a received wave, and processing means for calculating glucose level based on the phase shift and being in communication with the means for detecting.

According to a third alternate version of this embodiment, there may also be a heater and a sensor positioned on the device in close juxtaposition to the part of the subject's body to which said device is attachable. It may include means for communicating heat transfer characteristics to the processing means for calculating glucose level.

According to a third aspect of the invention, a device, for non-invasively measuring glucose level affixed to a part of a subject's body, comprises ultrasonic piezo elements positioned on opposing portions of the device and surrounding a part of the subject's body to which the device is attachable; and means for detecting a phase shift between a transmitted and a received wave.

It may preferably include a processing means for calculating glucose level based on said phase shift and being in communication with the means for detecting.

According to an alternate version of this embodiment, there may also be a heater and a sensor positioned on the device in close juxtaposition to the part of the subject's body to which said device is attachable. It may include means for communicating heat transfer characteristics to the processing means for calculating glucose level.

According to a fourth aspect of the invention, a device, for non-invasively measuring glucose level affixed to a part of a subject's body, comprises a heater and a sensor positioned on the device in close juxtaposition to the part of the subject's body to which the device is attachable; and means for communicating heat transfer characteristics to a processing means for calculating glucose level.

Other objects, features and advantages of the present invention will become apparent upon reading the following detailed description in conjunction with the drawings and the claims.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings, which illustrate examples of embodiments of the invention, in which:

DETAILED DESCRIPTION OF THE PREFERRED EMBODIMENT

Figure 1:
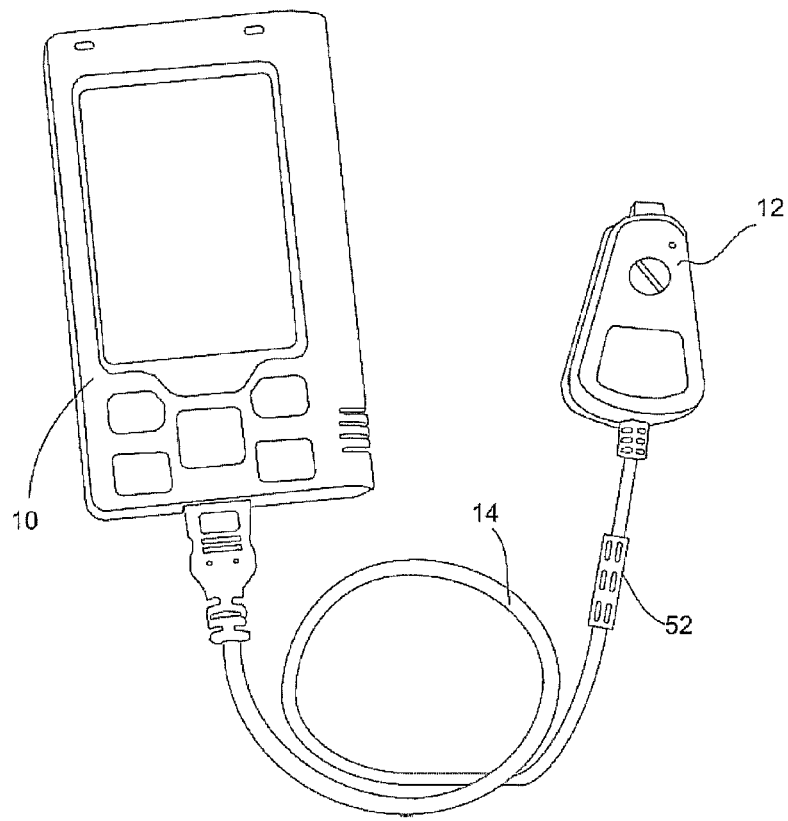
FIG. 1 is a view of the present invention, showing the Main Unit (MU) and the personal ear clip (PEC)

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The preferred embodiment of the system and its advantages are best understood by referring to the drawings and the following description where like numerals indicate like and corresponding parts of the various drawings. References to preferred embodiments are for illustration and understanding, and should not be taken as limiting.

While the herein description is with regard to a human patient, it may be appreciated that the herein device can be used to measure glucose in any subject, including animals.

In particular, the device includes a Main Unit 10 containing the software applications and an external unit 12 for affixment to the patient. Typically the external unit is placed on the patient's (or subject's or animal's) ear lobe, so the external unit will typically be configured as an ear clip.

A cable 14 is preferably used to provide a working connection between the Main Unit 10 and the external unit 12. It may be appreciated that wireless (for example, Bluetooth) technology may also be used, and the cable can be avoided.

It should be appreciated that the external unit 12 may be placed on any other suitable location of the subject's body, such as a toe, a finger, the web between the thumb and 2nd finger (forefinger). Generally it should be a body part that has skin and tissue characteristics similar to those of the ear lobe. When the external unit is placed on the body at a point other than the ear lobe, some adjustment of the algorithms may be necessary, as the skin and tissue characteristics are not uniform over the entire body.

Referring to FIG. 1, there is shown a unitary non-invasive device for measuring multiple glucose values and then obtaining a final glucose reading. In order to increase the accuracy of non-invasive glucose measurement, the device, according to the present invention, preferably uses a combination of more than one non-invasive methods, preferably three non-invasive methods: ultrasonic, electromagnetic and thermal. These methods account for the tissue's physiological response to glucose variations, resulting in changes of physical properties such as electric and acoustic impedance, as well as heat transfer (HT) characteristics of the cellular, interstitial and plasma compartments, due to changes in ion concentration, density, compressibility and hydration of both compartments.

As shown in FIG. 1, this non-invasive glucose monitor comprises a Main Unit (MU) 10, which drives a plurality of different sensor channels, preferably three different sensor channels (preferably one per technology), located on an external unit configured as a Personal Ear Clip (PEC) 12 (FIG. 1). In order to perform a spot measurement, the PEC 12 is clipped externally to the user's earlobe for the duration of the measurement (about a minute) and is removed afterwards. A cable 14 (or any well known wireless (for example, Bluetooth) technology) connects these two components of the device.

The unique aspect of the invention is that the (single) external unit 12 houses more than one measurement channel/protocol. More preferably it houses all elements to effect a plurality of separate and distinct non-invasive glucose measurements. Preferably, the external unit houses elements to effect three separate and distinct non-invasive glucose measurements by three separate and distinct technologies. This single external device provides the advantage, that only one single device has to be attached to the subject's body, which is convenient for a physician and/or a patient. In the preferred embodiment the external unit is configured as an ear clip 12.

It should also be appreciated and understood that each of the measurement channels is new and novel in and of themselves. Hence each measurement channel may be used in isolation by itself (or with still other measurement channels). By combining the three measurement channels in one unitary device, measurements are obtained from three separate and unique measurement channels, thereby optimizing the final reading.

Blood glucose variations affect Heat Transfer (HT) characteristics through changes of heat capacity (Zhao Z. Pulsed Photoacoustic Techniques and Glucose Determination in Human Blood and Tissue. *Acta Univ. Oul C* 169. Oulu, Finland, 2002), density (Toubal M, Asmani M, Radziszewski E, Nongaillard B. Acoustic measurement of compressibility and thermal expansion coefficient of erythrocytes. *Phys Med Biol.* 1999; 44:1277-1287) and thermal conductivity (Muramatsu Y, Tagawa A, Kasai T. Thermal Conductivity of Several Liquid Foods. *Food Sci. Technol. Res.* 2005; 11(3):288-294) of the tissue, due to water/electrolytes shifts (Hillier T A, Abbot R D, Barret E J. Hyponatremia: evaluating a correction factor for hyperglycemia. *Am J Med.* 1999 April; 106(4):399-403; Moran S M, R L Jamison. The variable hyponatremic response to hyperglycemia. *West J Med.* 1985 January; 142 (1):49-53). Thus, the alteration of the heat transfer processes that occur in a multi-layer sensor-tissue mechanical structure is a direct result of changes in glucose concentration (Wissler E H. Pennes' 1948 paper revisited. *J Appl Physiol.* 1998 July; 85(1):35-41). The higher the glucose concentration, the lower the heat capacity and the lower the thermal conductivity, thus causing greater temperature elevation in the exterior tissue layers in response to heating. Since the sensor(s) (e.g., thermistor(s)), according to the present invention, is (are) preferably mounted/affixed on the epidermis layer, the measured rate and magnitude of the temperature change upon heating is greater than in the internal tissues.

The Thermal method, according to the present invention, applies a specific amount of energy to the tissue. Preferably both the rate and/or the magnitude of the temperature change, caused by the application of the known amount of energy to the tissue, are functions of the heat capacity, density and thermal conductivity of the tissue. Thus, the device according to the present invention provides means such that the glucose level is preferably evaluated indirectly by measuring changes in the HT characteristics, obtained after tissue heating for a predetermined duration of time.

Figure 2:
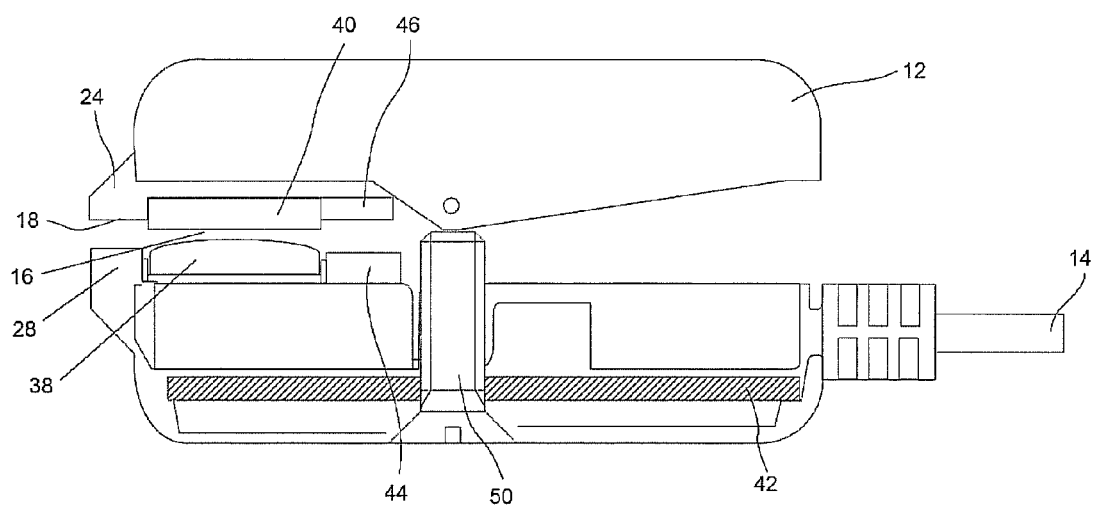
FIG. 2 is a side view, partially broken away and in section, of the PEC.
Figure 3:
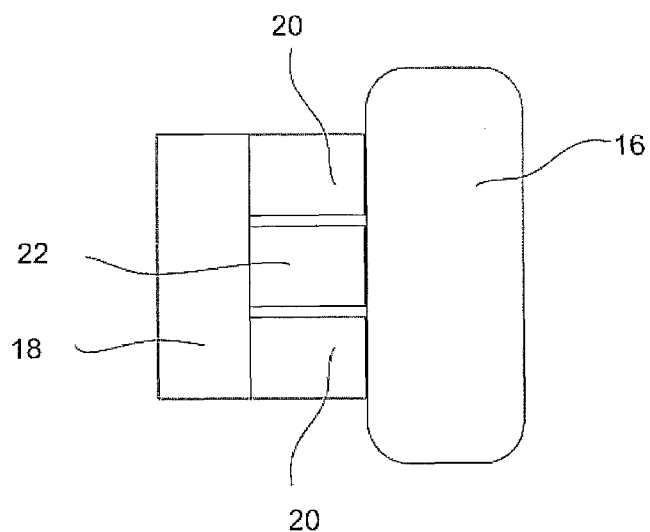
FIG. 3 is a view of Sensor-tissue structure for one embodiment of the Thermal channel of measurement.
Figure 17A:
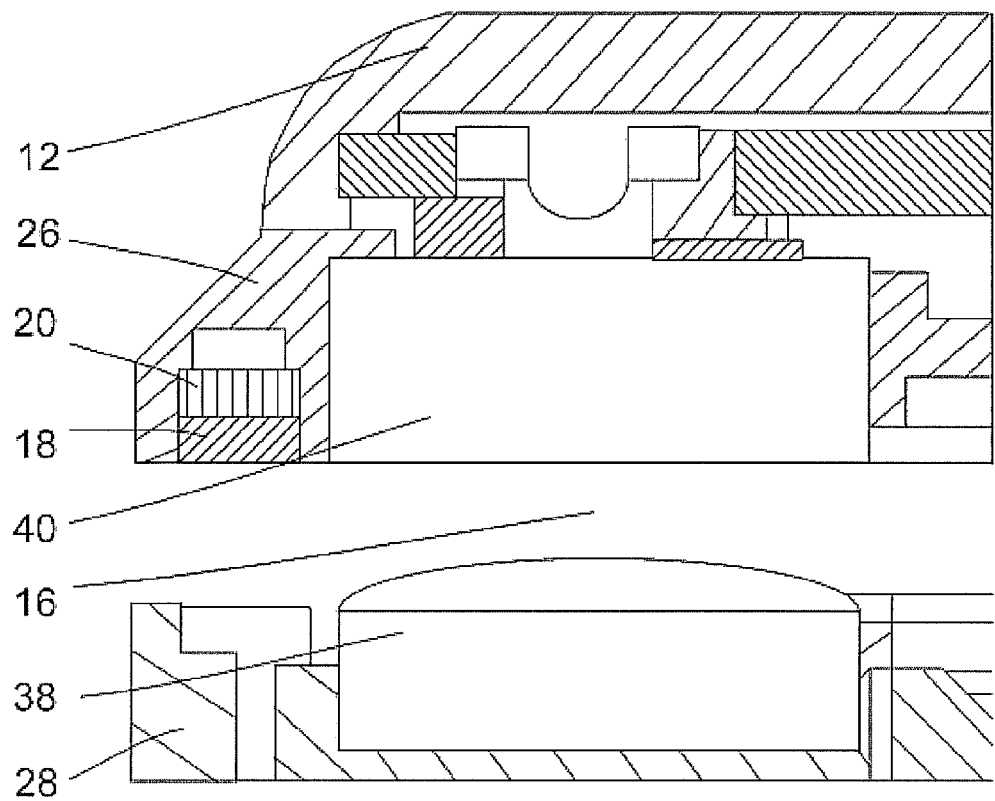
FIG. 17A is an enlarged side cross sectional view of the tip of the ear clip and showing the elements constituting the measurement channels.
Figure 17B:
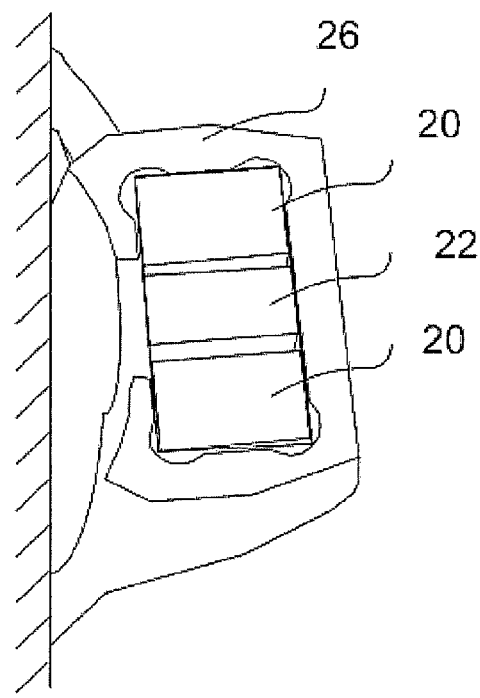
FIG. 17B is an enlarged top cross sectional view of a portion of the tip of the ear clip.

FIG. 3 shows a sensor-tissue structure, according to a preferred embodiment of the present invention. A bottom plate serves as a heater 18 and heat conductors 20 are included (see FIG. 17). A thermal sensor 22 is located in the middle between the conductors 20. As shown in FIG. 2, the thermal sensor is located on the tip 24 of the ear clip (PEC) 12.

Figure 12:
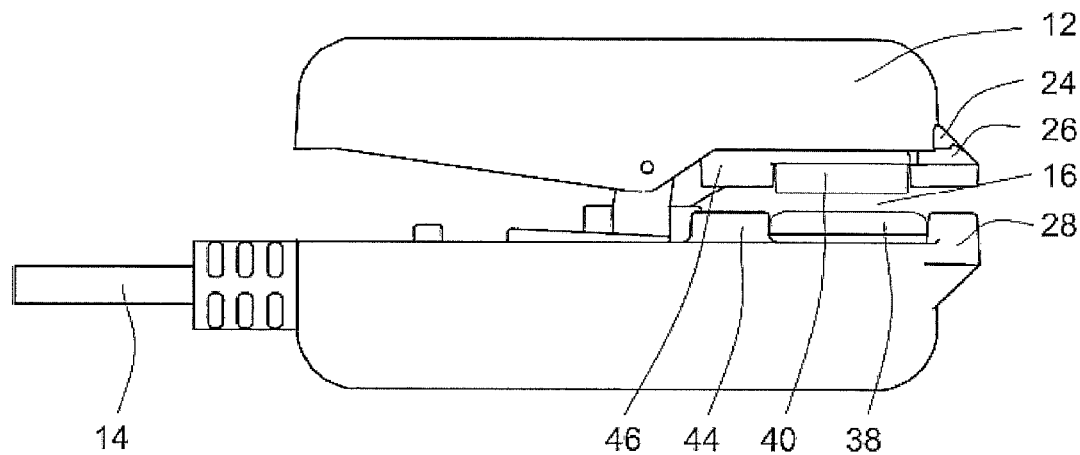
FIG. 12 is a side view of the ear clip.
Figure 13:
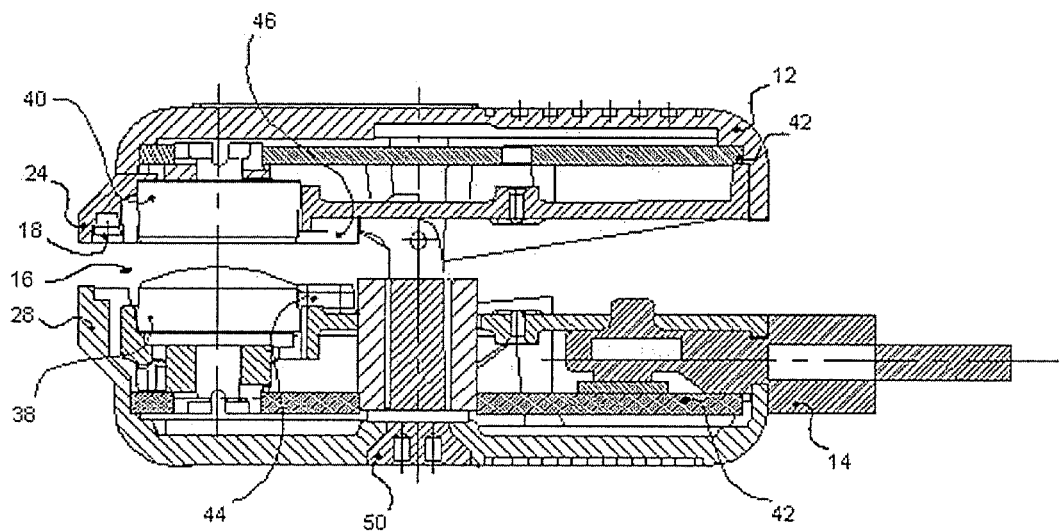
FIG. 13 is a side view, broken away and partially in section, of the ear clip.

Referring now to FIGS. 12 and 13, the thermal module, which preferably comprises a thermistor 22, a heater 18 and conductors 20, located on an ear 26 extending from the end of one side of the ear clip 12 (e.g. on the first portion of the ear clip). The opposing surface 28 (i.e., the second portion of the ear clip) is preferably empty with no thermistor elements. In other words, it is preferred when the heater 18 and the thermal sensor 22 are located on the same side of the ear clip. In particular, it is preferred that the heater 18 and the thermal sensor 22 are located on the same side with regard to a ear lobe, when the external unit 12 is attached to the ear lobe.

Figure 14A:
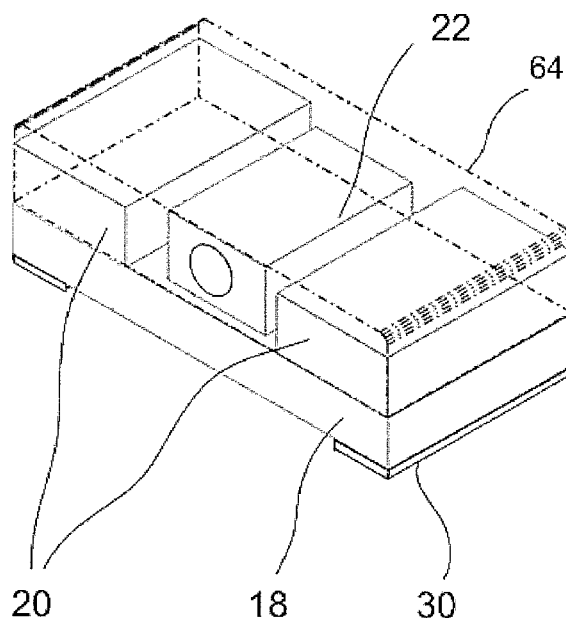
FIG. 14A is a perspective view of the elements of the thermal channel.
Figure 14B:
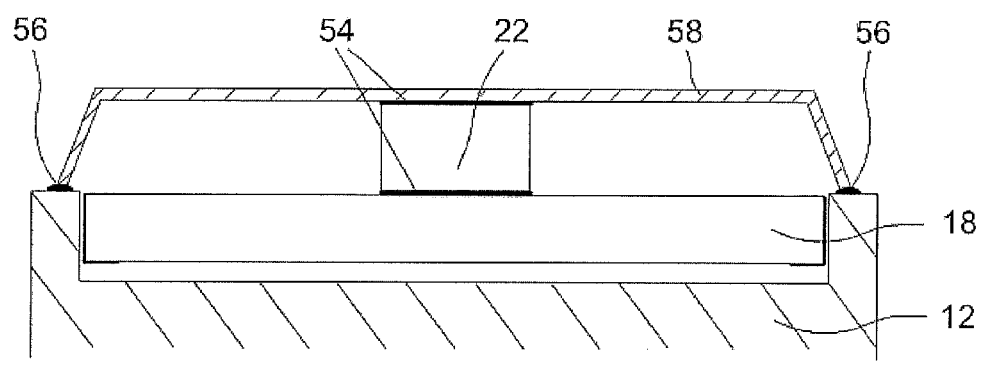
FIG. 14B is an end view, partially in section, of the elements of an alternate embodiment of the thermal channel.
Figure 14C:
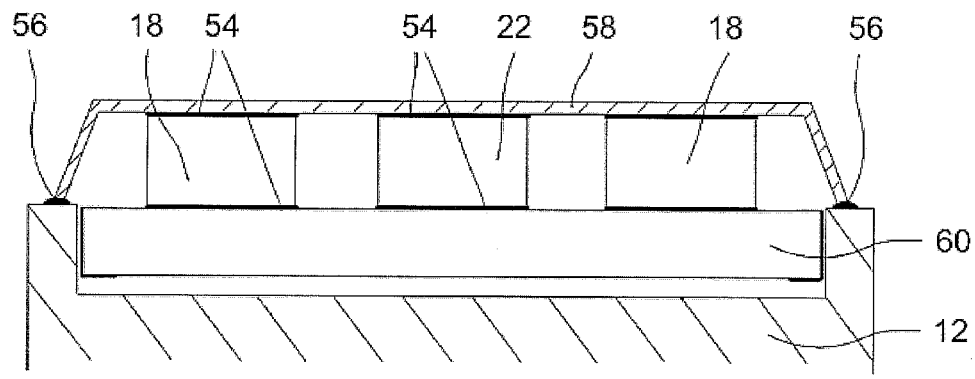
FIG. 14C is a view similar to FIG. 14b and showing an alternate embodiment.

As depicted in FIGS. 14A, 14B and 14C, the heater 18 is preferably made as a plate or block and is preferably constituted by a resistor. Two plates 20 are secured to the top of the plate to conduct heat energy and serve as the conductors 20. This may be done by adhering, gluing or bonding or any other suitable means. Preferably the conductors 20 are aluminum, but any heat conducting material may be used. On the bottom of the plate, preferably soldering pads 30 are provided which may be used to connect the heater 18 to integrated circuit boards 42 (see FIG. 13). Preferably, a housing contains all the sensor (e.g. thermistor) modular components. Ideally for a 4 Volt system, the resistor (e.g. the heater plate) has a resistance between 23 and 43 Ohms and is preferably 33 Ohms. It generates heat in the range of about 15°-45° C. and is preferably about 42-45° Centigrade. Any suitable heat sensor may be used.

The heater sends heat energy into the ear. It begins the heating process at standard ambient temperature 15-35° C. Usually the surface of the ear lobe is a little warmer at 28-32° C. The power of the heater provides preferably a maximum of 0.5 Watt and preferably a minimum of 0.1 Watt. According to other preferred embodiments, however, heaters with smaller hear energy may be used which preferably heat for longer times. Also a heater with a larger heat energy may be used which preferably heat for a shorter time.

As may be appreciated, the thermistor module should be small enough to fit on the tip of the ear clip. Preferably the resistor plate, constituting the heater 18, is about 5 millimeters long, 0.6 millimeters thick and 2.4 millimeters wide. The conductors 20 are preferably 1.5 millimeters long, 0.7 millimeters thick and 2.4 millimeters wide. As for the sensor 22, it is preferably 1.30 millimeters long, 0.8 millimeters thick and 2.0 millimeters wide. These are standard elements available in the marketplace; and, hence the standard available sensor is not as wide as the resistor plate and conductors and extends slightly above the conductors. A small difference in the overall dimensions is not critical.

There are several possible embodiments for the thermal channel. One preferred embodiment is shown in FIG. 14A. This embodiment consists of the thermo-sensor (thermistor) 22, the heater 18 and the thermo-conductors 20. The surface of the thermal module, which contacts the earlobe, is coated with a thermo-conductive biocompatible coating 64. When the heater 18 is switched on, heat flux passes through the thermo-conductors 20 and the thermistor 22 through the coating to the earlobe (or other part of the body). The heat absorption of the earlobe depends on the glucose level. The thermistor 22 measures the changes of temperature in the earlobe, which is influenced by the heating intensity and the absorption of the ear lobe. This temperature is used for analysis by data processing and to determine the glucose level.

FIG. 14B represents another preferable embodiment of the thermal channel. It consists of the thermo-sensor (thermistor) 22, the heater 18 and a metal membrane 58, which has high thermo-conductivity. These components—the membrane 58, the thermistor 22 and the heater 18—are glued together with a thermo-conductive adhesive 54. Preferably, the membrane 58 is adhered to the PEC 12 with an adhesive 56. The outer surface of the membrane 58 has good thermal contact with the earlobe. When the heater 18 is switched on, heat flux passes through the thermistor 22 and the membrane 58 to the earlobe (or other part of the body). The temperature change of the earlobe depends on the glucose level, and the thermistor 22 measures the changes of temperature in the earlobe, which is used for data processing and determining the glucose level.

A third preferable embodiment of the thermal channel is shown in FIG. 14C. It consists of the thermo-sensor (thermistor) 22, two heaters 18, the printed circuit board (PCB) 60 and the metal membrane 58, which has high thermo-conductivity. These components—the membrane 58, the thermistor 22 and the heaters 18—are adhered with thermo-conductive adhesive 54. Preferably, the membrane 58 is glued to the PEC 12 with an adhesive 56. The heaters 18 and the thermistor 22 are soldered onto the PCB 60. The outer surface of the membrane 58 has good thermal contact with the earlobe. When the heaters 18 are switched on, heat flux passes through the membrane 58 to the earlobe (or other part of the body). The temperature change of the earlobe depends on the glucose level, and the thermistor 22 measures the changes of temperature in the earlobe, which is used for data processing and determining the glucose level.

Figure 4:
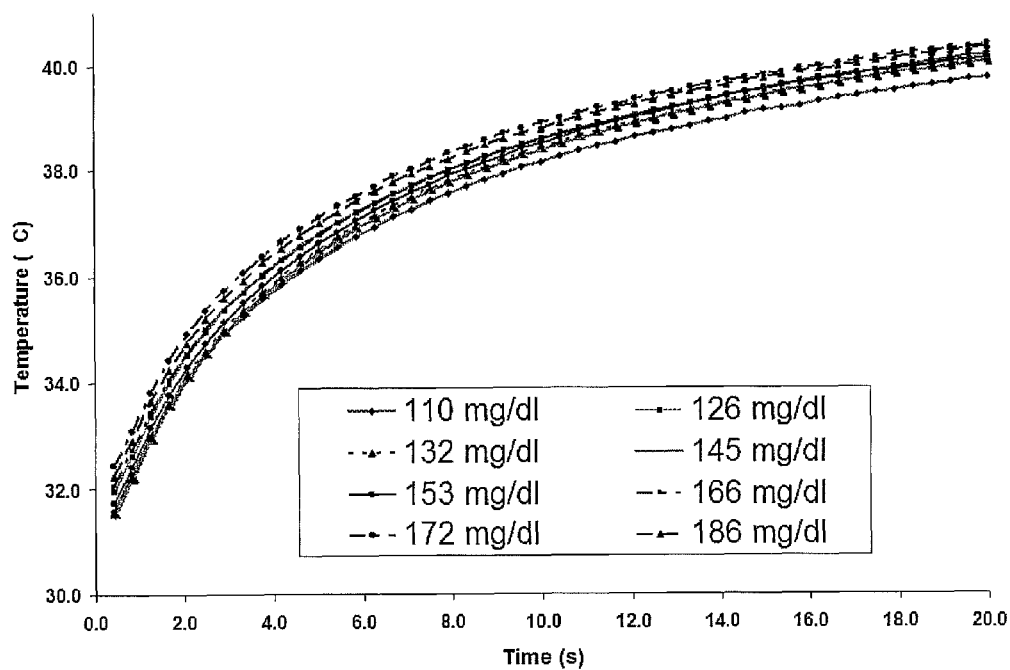
FIG. 4 is a graph showing the raw process of heating the sensor-tissue structure in a subject, reflecting different glucose levels.

FIG. 4 depicts the raw process of heating the sensor-tissue structure in a subject. The different curve shapes of the heating process represent different glucose concentrations. Temperature is represented in degree Celsius in FIG. 4.

Ambient temperature that defines the boundary condition of the surface skin temperature and the sensor's initial temperature have influence on the process as well. Therefore, the thermal process is integrated and normalized to consider the initial skin surface temperature, followed by a compensation for the difference between the ambient and skin temperatures (Equation 1). The integrated, corrected and compensated signal (Heat signal) is shown in FIG. 5, as a function of glucose concentration.

$$\text{Heat\_signal} = \left[ \int_{t_0}^{t_f} F(\text{Heat\_process}) dt - T_{ear} \cdot (t_f - t_0) \right] - k \cdot (T_{ear} - T_{amb}) \quad (\text{EQ. 1})$$

where $t_0$ and $t_f$ are the starting and the finishing time of the heating process; $T_{ear}$ and $T_{amb}$ are the tissue and the ambient temperatures, accordingly and k is the temperature correction factor.

Figure 5:
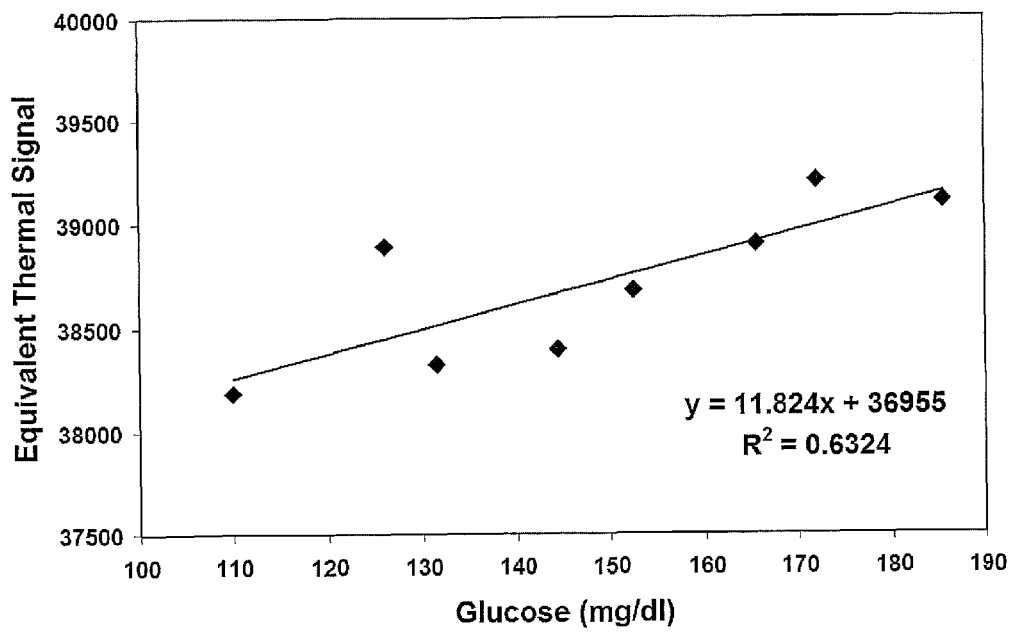
FIG. 5 is a graph showing integrated and temperature-corrected equivalent thermal signal in a subject versus glucose level.

FIG. 5 shows an integrated and temperature corrected heat signal in a subject versus glucose level.

Changes in the glucose concentration can be indirectly evaluated by measurement of the sound velocity through the tissue. As glucose concentration increases, the propagation velocity increases as well (Zhao Z. Pulsed Photoacoustic Techniques and Glucose Determination in Human Blood and Tissue. *Acta Univ. Oul C* 169. Oulu, Finland, 2002; Toubal M, Asmani M, Radziszewski E, Nongaillard B. Acoustic measurement of compressibility and thermal expansion coefficient of erythrocytes. *Phys Med Biol.* 1999; 44:1277-1287; U.S. Pat. No. 5,119,819). Since the propagation velocity depends linearly on glucose concentration, the higher the glucose content in a tissue, the faster the ultrasonic wave propagates through it, thus decreasing the time of propagation.

The Ultrasound measurement channel consists, in a preferred embodiment, of piezo elements, specifically an ultrasound transmitter 34 and an ultrasound receiver 36, attached (or attachable) near the subject's ear lobe 16. Preferably an electronic circuit is also provided for the Ultrasound measurement channel. The transmitter 34 (ultrasound piezo element) is located in the external device, such that (when the external device is attached to the ear lobe) a continuous ultrasonic wave produced by the transmitter travels through the ear lobe with characteristic velocity, causing a phase shift ($\Delta\phi$) between the transmitted and received wave (FIG. 6B).

Figure 6A:
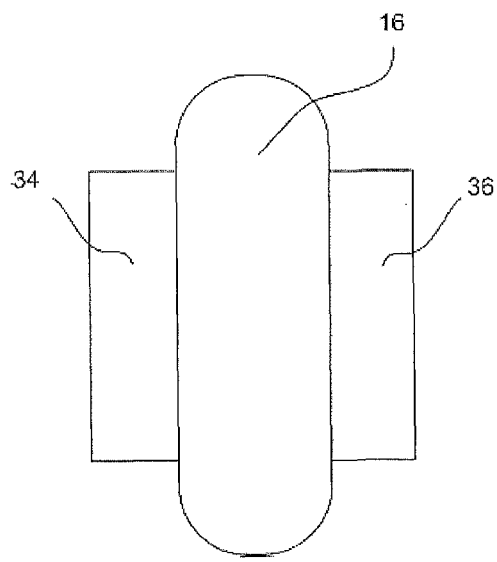
FIG. 6A is a schematic representation of the earlobe between the two ultrasonic piezoelements for the Ultra Sound channel of measurement.
Figure 6B:
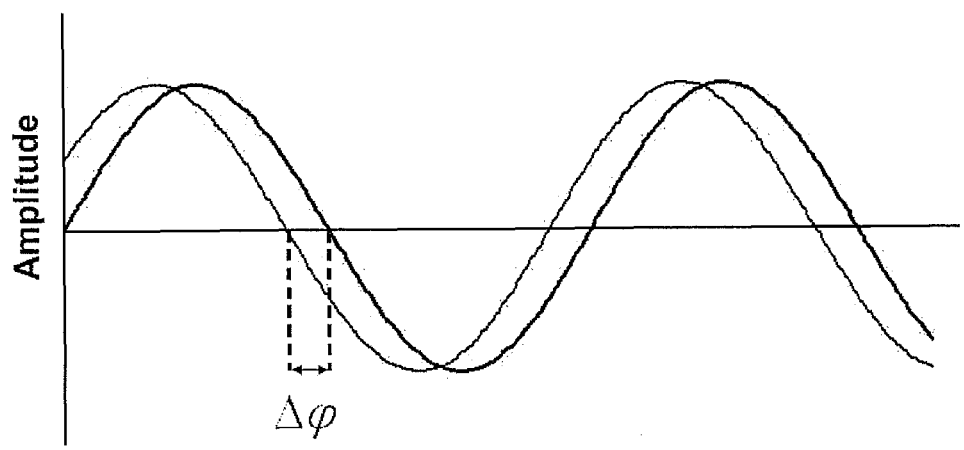
FIG. 6B is a graph showing the Phase shift between the received and transmitted waves, measured as $\Delta\phi$.

The piezo elements—transmitter 34 and receiver 36 (optionally followed by an amplifier)—are arranged one on each side of a subject's ear lobe (see e.g. FIG. 6A). The main unit (MU) 10 sends a signal to the transmitter 34 to transmit a signal. After propagating through the ear lobe 16, the receiver 36 steps up the received signal and sends it back to the MU 10 for processing with an algorithm to get the corresponding value of glucose.

On opposing sides of the ear clip 12, the piezo elements—the transmitter 36 and the receiver 34—are disposed. Generally, these ultra sound elements are sensitive to mechanical pressure. In order to protect the elements and to maintain the efficacy of the elements, membranes 38 and 40 are preferably placed over the ultra sound elements (see FIGS. 15 and 16). Preferably, an ultrasound—conductive adhesive or glue, such as epoxy, is placed between the membranes and the ultra sound elements to hold the membranes firmly on the ultrasound elements. Generally the adhesive or glue or epoxy should be suitable for conducting ultrasound waves, so there is minimal signal loss. A layer of 0.05 mm is generally adequate for the adhering material.

Since the ultrasound piezo elements are also disposed in the ear clip, here again they should be made small. They may be any suitable size, but preferably the ultra sound elements are round and about 9.0 millimeters in diameter and less than 3.0 millimeters in thickness in the preferred embodiment shown herein. The membranes 38, 40 are preferably made round and have a diameter of about 9.5 millimeters. It may be appreciated that any size is acceptable as long as it fits in the ear clip.

An electrically conductive and biocompatible coating is preferably placed on the outer surface of the membrane 38, 40 to enhance propagation of the signal. Typically a coating of 0.01 mm is adequate.

The membranes may preferably be made of nickel, which is generally a biologically stable and conducts signals well. Any other suitable material, such as gold or titanium, may be used.

Preferably, the membranes 38, 40 are made of copper with a nickel coating. In an alternate embodiment, the membranes may be made of stainless steel and no coating would be needed.

In the preferred embodiment, it has been found that it is advantageous if one membrane 40 is flat and the other 38 is convex. This "hybrid" combination provides the best solution from a fitting point of view, and securely holds the device on the subject's ear lobe.

Frequencies can range from 180 K Hertz (180 KHz) up to 1 Mega Hertz (1 MHz) and signal amplitudes may vary from 0.5 volt to 3 volts. The received signal amplitude may vary between 5 mV and 50 mV. Preferably the receiver amplifies the signal by about 20 times.

Figure 15:
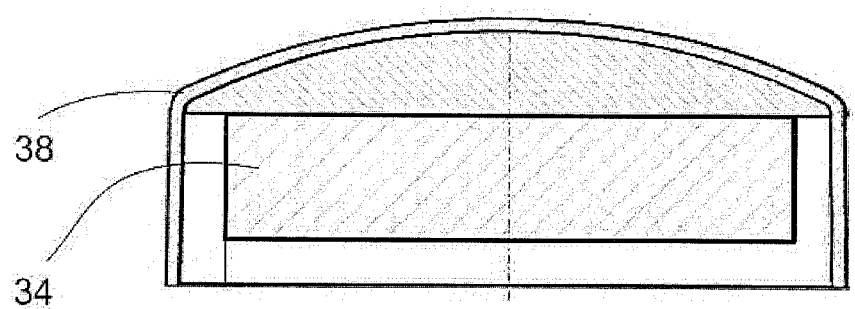
FIG. 15 is a side view in cross section of a first membrane for the ultrasound transducer, which preferably also serves as one of the plates of the capacitor for the electromagnetic channel.
Figure 16:
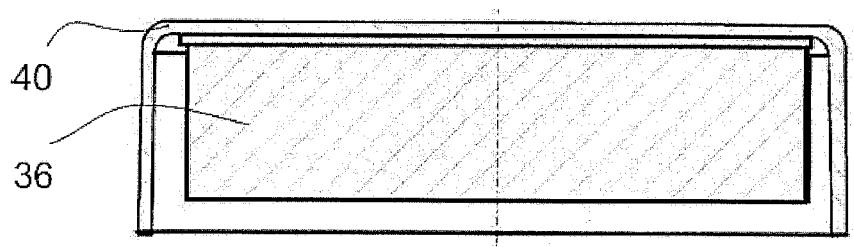
FIG. 16 is a side view in cross section of a second membrane for the ultrasound transducer, which preferably also serves as one of the plates of the capacitor for the electromagnetic channel.

As illustrated in FIGS. 15 and 16, the ultra sound piezo elements preferably fit into the respective membranes with the adhesive (or epoxy) layer between them.

The velocity is phase-related (Equation. 2):

$$V = (f \times d) \times 2\pi / \Delta\phi \quad \text{(EQ. 2)}$$

where f: frequency (Hz); $\Delta\phi$: phase shift (radians); and d: distance between piezo-elements of the sensors (m).

During calibration, two optimal frequencies are elected, one from a low frequency range and one from a high frequency range, where the frequency ranges are non-overlapping. After calibration, the measurements are conducted at the two chosen frequencies.

Figure 7:
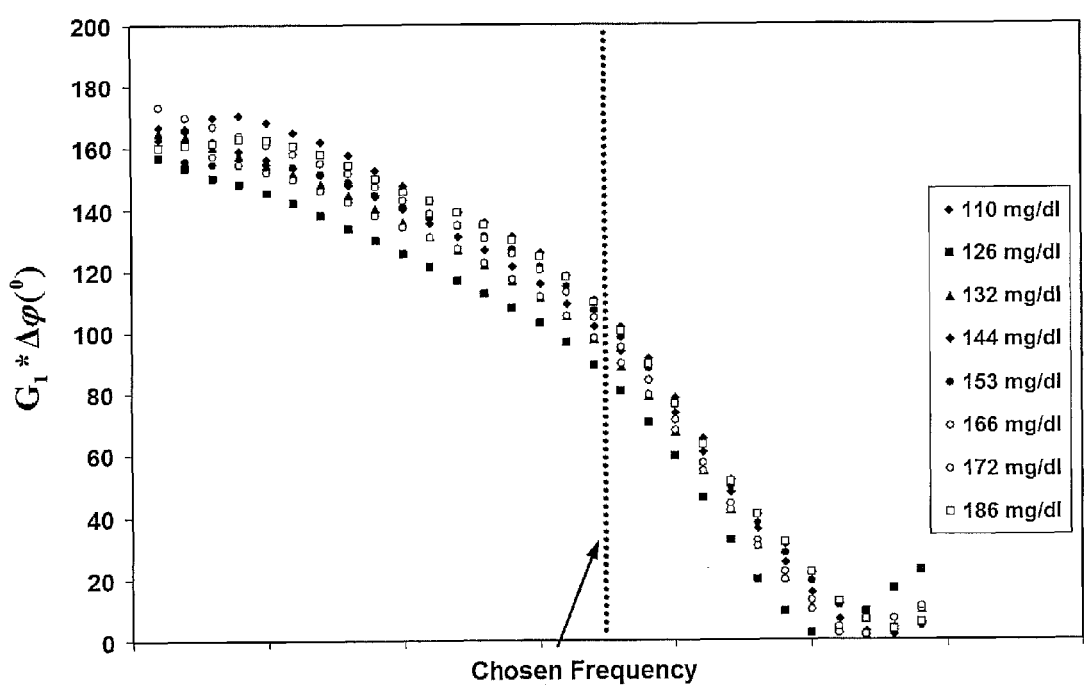
FIG. 7 is a graph showing the phase shift versus input transducer frequency in the low frequency region; and, the amplified phase-shift values are viewed at a chosen frequency, which was found to be the optimal frequency during calibration for a subject.

FIG. 7 presents a graph of the measured phase-shift values as a family of functions having the frequency of excitation as an argument and the glucose value as a parameter of the family. The tissue thickness determines the part of the measured phase shift cycle (ascending or descending). In the arrangement shown in FIG. 7, the descending part of the cycle is viewed, causing $G_1 \times \Delta\phi$ to increase with enhancement in glucose level.

This graph in FIG. 7 shows the phase shift versus input transducer frequency in the low frequency region. The amplified phase shift values are viewed at chosen frequency, which was found to be the optimal frequency during calibration for a subject. Different curves on the graph apply to different glucose levels.

It is well known that the velocity of ultrasound waves depends on the propagation medium temperature (U.S. Pat. No. 5,119,819; Zips A, Faust U. Determination of biomass by ultrasonic measurements. *Appl Environ Microbiol*. 1989 July; 55(7):1801-1807; Sarvazyan A, Tatarinov A, Sarvazyan N. Ultrasonic assessment of tissue hydration status. *Ultrasonics*. 2005; 43:661-671). The ambient temperature affects the sensor parameters, whereas the tissue temperature impacts the wave propagation in the tissue itself. Therefore, temperature correction, using both ambient and tissue temperatures is necessary. The temperature correction is performed on the measured amplified phase shift (FIG. 8), using the following formula (Equation. 3):

$$\text{Phase\_shift\_cor} = \text{Phase\_shift} \pm G_2 \times \left(1 - \frac{T_{amb}}{T_{ear}}\right) \quad \text{(EQ. 3)}$$

where Phase_shift_cor is the temperature corrected amplified phase shift; $G_2$—correction factor; $T_{amb}$—ambient temperature; and $T_{ear}$—earlobe surface temperature. The sign of correction depends on the direction of the phase shift change with frequency.

Figure 8:
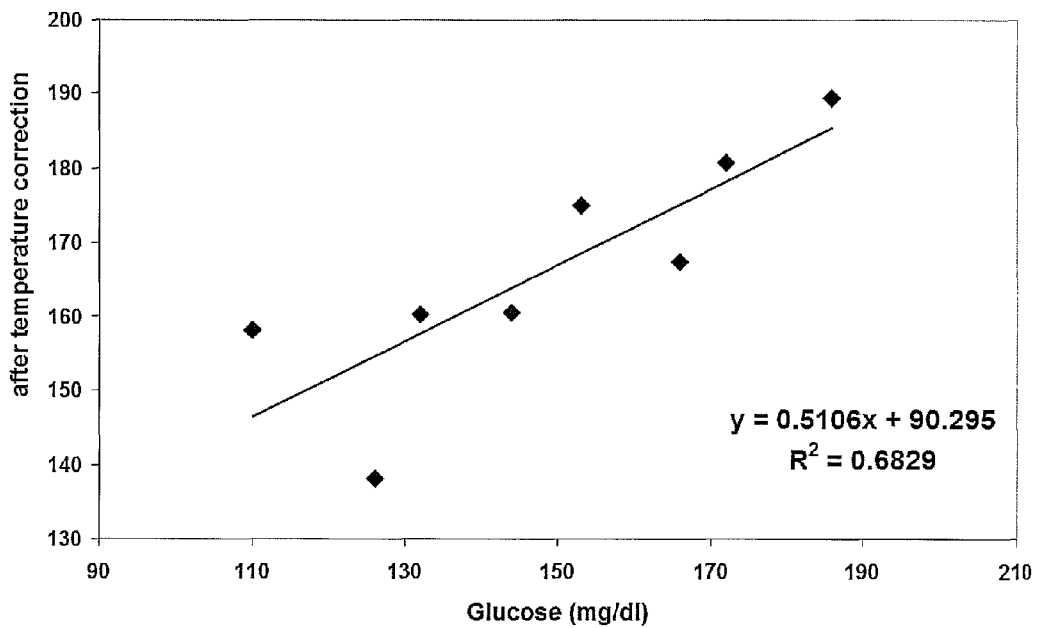
FIG. 8 is a graph for a subject, in the Ultrasonic channel, showing phase shift (measured at chosen frequency), corrected for temperature vs. glucose level.

FIG. 8 is a graph showing the phase shift (measured at chosen frequency) vs. glucose, corrected for temperature for a subject.

A glucose-induced water and ion transport across the cellular membrane leads to changes in the electrical properties of the cellular and consequently extracellular compartments (Genet S, Costalat R, Burger J. The Influence of plasma membrane electrostatic properties on the stability of cell ionic composition. *Biophys J*. 2001 November; 81(5):2442-2457; Hayashi Y, Livshits L, Caduff A, Feldman Y. Dielectric spectroscopy study of specific glucose influence on human erythrocyte membranes. *J Phys D: Appl Phys*. 2003; 36:369-374). Primarily, the change in the dielectric properties is observed (Gudivaka R, Schoeller D, Kushner R F. Effect of skin temperature on multi-frequency bioelectrical impedance analysis. *Appl Physiol*. 1996 August; 81(2):838-845), which, consequently is reflected in changes of the whole tissue impedance. To reflect changes in the tissue electrical impedance caused by varying glucose, the electromagnetic channel (EMC) includes a special auto-oscillating circuit and the earlobe, which functions as a dielectric material, positioned between two electrodes connected to the circuitry (FIG. 9).

Figure 9:
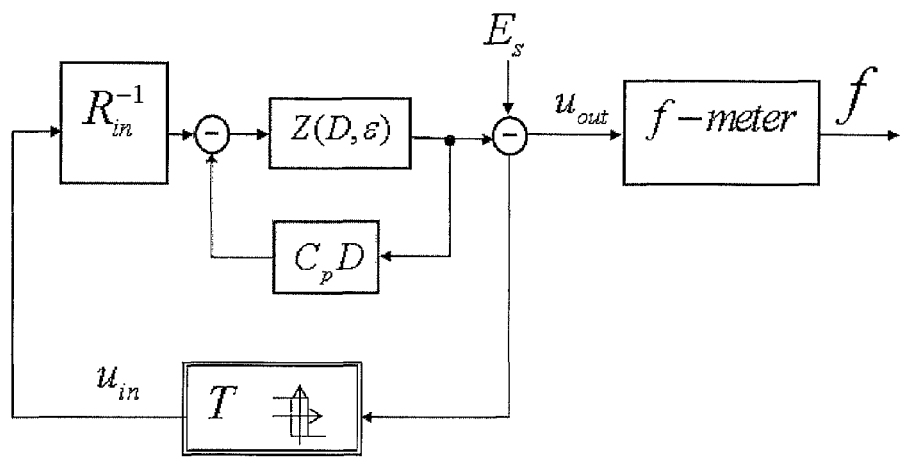
FIG. 9 is a schematic showing the Electromagnetic Channel.

FIG. 9 shows the Electromagnetic Measurement Channel (EMC) wherein $R_{in}$—Input resistance; $Z(D,\in)$—Transfer operator of the sensing element—an EMC integrator including the earlobe tissue in the feedback; the transfer operator time constants depend on the tissue electric permittivity denoted $\in$;

$$D = \frac{d}{dt};$$

$C_p$—Parasitic capacitance; f-meter—Auto-oscillation frequency (f) measuring circuit; T—Relay element with hysteresis creating a positive feedback in the auto-oscillating circuit; $E_s$—Electrical potential on the skin surface The same membranes 38 and 40 used for the ultrasound channel may preferably also serve as capacitor plates and the earlobe 16 serves as the dielectric. An oscillator is used to generate signals and these signals depend on the parameters of the ear lobe. Frequencies may range from 5 K Hertz (5 KHz) up to 100 K Hertz (100 KHz) and the amplitudes vary from about 0.1 volts to 1.5 volts.

Figure 10:
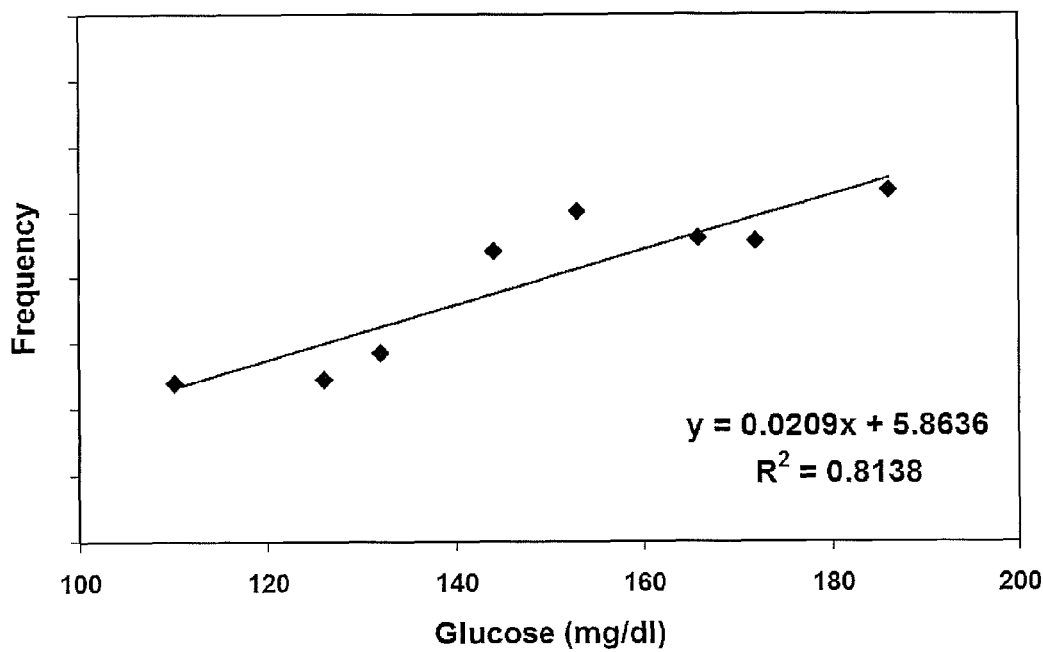
FIG. 10 is a graph showing Electromagnetic signal (frequency) corrected for temperature versus glucose level, for a subject.

The earlobe temperature is also considered in the measurement, since tissue impedance is temperature dependent (Gudivaka R, Schoeller D, Kushner R F. Effect of skin temperature on multi-frequency bioelectrical impedance analysis. *Appl Physiol.* 1996 August; 81(2):838-845). Among the disturbance-representing variables of the EM Channel, the ambient temperature plays two roles: a) influencing the tissue parameters; b) affecting the sensor's electromagnetic parameters such as parasitic capacitance of electrodes. Therefore the electromagnetic signal is corrected for both, ambient and ear temperatures, using Equation 4, as shown in FIG. 10.

$$\text{Electromagnetic\_signal\_cor} = \text{Electromagnetic\_signal} - D \times \left(1 - \frac{T_{amb}}{T_{ear}}\right) \quad \text{(EQ 4)}$$

where: Electromagnetic_signal_cor is a temperature corrected electromagnetic signal (self-oscillation frequency); D—correction factor; $T_{amb}$—ambient temperature; and $T_{ear}$—earlobe surface temperature.

In a preferred embodiment, there is also a distance sensor on the ear clip (PEC) 12—a magnet 44 on one side and a sensor 46 on other side. The sensor 46, preferably a magnetic field measuring sensor, measures magnetic field intensity to ensure the distance between the membranes is the same as at a calibration stage.

Figure 11:
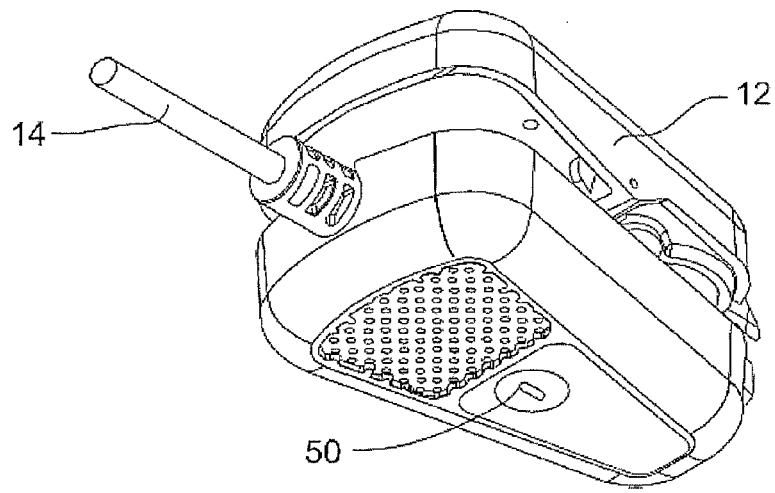
FIG. 11 is a perspective view of the ear clip.

FIG. 11 shows the preferred embodiment of the ear clip 12. Preferably it is made of ABS plastic, but any suitable material will be effective. The size is dependent on the earlobe size of the subject. In a preferred embodiment, it is preferably about 25 millimeters long and about wide. It may be tapered. Preferably there will be different size clips to accommodate subjects of different sizes of earlobes.

As is well known for clips, preferably one side pivots about the other. One side has a pivot pin which fits into an appropriate seat in the other piece of the ear clip. A spring is used for biasing.

Preferably, an ambient temperature sensor 52 is also provided which may be located at the external unit 12, the main unit 10 and/or may be placed on the cable 14 (see FIG. 1).

Preferably, as is common in modern electronic devices, integrated circuit boards 42 are mounted within the ear clip 12 (see FIG. 13). The aforesaid components of the three channels—ultrasonic, electromagnetic and thermal—are mounted on them. Then, either through the cable or through wireless technology (such as Bluetooth), communication is established with the Main Unit. As required, the Main Unit issues signals for activating each measurement channel and for then collecting data and thereafter calculating the glucose value.

Preferably, there is calibration performed prior to glucose measurements, so that the influence of individual quasi-stable factors, such as tissue structure, can be minimized. The sensor is individually adjusted for optimal fit, according to the thickness of the user's earlobe, prior to calibration. Preferably an adjustment screw 50 (FIGS. 2, 14 and 16) is used to adjust the distance between the sensors and consequently the pressure on the earlobe for optimal fit. This action may be guided by the Main Unit 10. The optional distance sensor 44, 46 preferably assures this preset distance is maintained.

After adjusting the ear clip (PEC) 12, the calibration process begins. One preferred procedure for calibration is set forth herein.

The calibration procedure consists of correlating invasive basal and post-prandial blood glucose data, taken from fingertip capillary blood, with six sequential measurements with both the device and an invasive device used as a reference, generating a calibration curve that is exclusive to each individual.

The first three calibration points are performed at the same (fasting) glucose level and help establishing a rather accurate initial point for the model used in the calibration. They are performed in fasting state, consisting of one invasive and three consecutive non-invasive measurements, followed by food and drink consumption, in order to increase blood glucose by at least 30% from the fasting value but no less that 30 mg/dl. In some cases this may be done in a non-fasting state. 20 minutes post meal, a set of five sequential measurement pairs, with time intervals of about 10 minutes in between is taken. In total, the calibration process takes about 1.5 to 2 hours.

At the first point of calibration, the distance is automatically measured (by means of the optional distance sensor 44, 46 provided in the ear clip 12 or by using an alternative method) and set as a reference distance (original location or preset reference point) of the sensors, which, in the following calibration points, as well as measurement points will be checked, prior to beginning the measurements. The earlobe is a generally parallel tissue with homogeneous surface. Therefore, if the distance in any of the calibration points, or in a regular measurement points differs (within a certain tolerance range) from the preset reference point, the user is guided by the device to move the PEC 12 as required, in order to get to the reference distance. Once the calibration is completed, a vector of individual linear model's parameters is set for each technology's output.

For the thermal technology, heating intensity is checked during the measurement of the first point and a correction factor is calculated for optimal heating intensity, to be used in the consequent measurements. This factor is individually calculated for each user, in order to assure increasing the tissue surface temperature above a minimal increment threshold.

For the electromagnetic technology, the oscillations are performed at three close but different frequency ranges. The optimal frequency range is chosen as a function of individual sensitivity to glucose changes during calibration. Furthermore, the maximal and minimal deviations between the working frequency range and the next close frequency range are set as threshold values for the electromagnetic signal validity filter (Equation 5):

$$EM_{min} < \frac{EM_i}{EM_j} < EM_{max} \quad \text{(EQ. 5)}$$

where: $EM_{min}$ and $EM_{max}$ are minimal and maximal electromagnetic signal threshold values, accordingly; $EM_i$—the electromagnetic signal in the working frequency range; and $EM_j$—the electromagnetic signal in the neighboring frequency range.

In order to choose optimal working frequencies for the acoustic measurement method, a sweeping of 2 frequencies' regions is performed in the low and high frequency regions, during calibration. In each region, the optimal frequency is selected, according to the signal's amplitude (the strength of propagated signal) and the sensitivity of the phase shift to glucose changes at that particular frequency. Post calibration, the measurements are performed at these 2 selected frequencies (one from the low region and one from the high region)

At each calibration point, it is preferred that both ambient and tissue temperatures are taken. At the end of the calibration process, a correlation between the two temperatures is found. This correlation is later used to discover discrepancies in the measured ear and ambient temperatures for each measurement.

After the calibration, glucose spot measurements can be performed by clipping the ear clip 12 to the earlobe for the duration of the measurement (about 1 minute) and removing it afterwards.

Following the sensor's positioning verification (by the device), using the distance reference established during adjustment, the measurement begins. Each measurement channel produces several outputs, upon which three stages signal processing is applied: signal validation and recognition of outliers; temperature compensation and temperature correction.

In the first stage for the Ultrasonic channel, the signal's amplitude for each elected frequency is checked, to ensure proper wave propagation through the tissue.

Since the electromagnetic and ultrasonic sensors are physically mounted on the same area of the tissue, a low measured amplitude points out a poor contact quality. In this case the measurement is disregarded and a failure notice is provided to the user. In the thermal technology, the sensor is mounted on a different tissue area than the electromagnetic and ultrasonic sensors. Therefore, a good quality contact for the two later technologies does not guarantee the same for the thermal channel. Thus, the heating process is also checked for minimal and maximal temperature threshold rise, through a validity filter. Out of range rise is regarded as poor contact quality and produces a failure notice to the user. The electromagnetic channel output is also checked for maximal and minimal deviations between the working frequency range and the adjacent one, as discussed in the calibration section.

Since both ambient and the tissue temperatures are used for compensation in every measurement channel, they should be checked for validity first. Therefore, in the second stage, the temperatures are tested on correlation relatively to calibration. Therefore, for each measurement, low correlation indicates interference in one of the measured temperatures. The disturbed temperature is first compensated according to the other temperature, and then both are used for signal temperature correction, orchestrated across all three technologies.

The third stage includes temperature correction for all the technologies' outputs, as discussed earlier. Furthermore, glucose value is calculated for each measurement channel, using the model coefficients which were established within the calibration procedure.

The received glucose values from each measurement channel are checked for correlation. Subsequently, weights are assigned to each of the three values, according to the degree of correlation. Finally, a weighted combination of the three technologies outputs produces a more accurate glucose reading.

Glucose and other blood solutes influence different tissue properties such as conductivity, permittivity, heat capacity, density and compressibility in different tissue compartments (e.g. interstitium, blood, cells). Thus, measuring such properties can lead to evaluation of the BG level in a human body.

Generally, non-invasive devices (in development stages) producing either trend analysis or continuous glucose values, measure physiological phenomena that are reflected by changes in the tissue parameters, correlating with blood glucose (Khalil OS. Non-invasive glucose measurement technologies: An Update from 1999 to the Dawn of the New Millennium. *Diabetes Technol Ther.* 2004 October; 6(5):660-697; Smith J L. The Pursuit of Noninvasive Glucose: "Hunting the Deceitful Turkey". 2006). However, the actual glucose value derived from such correlation is different than the real glucose value, since factors, other than glucose, influence tissue parameters as well. These disturbing factors decrease the signal to noise ratio and cause inaccuracies in readings.

In order to minimize the impact of those disturbances, a methodology combining multi-technology and multi-sensors is suggested. Each technology measures different tissue parameters that are affected by the same change in glucose concentration. Thus, each method per se is indicative of glucose, but is confined by the impact of interfering factors, due to lack of specificity. Therefore, a simultaneous evaluation of the mentioned physiological changes through measurement of different sets of tissue perturbations, induced by changes in glucose concentration, is expected to increase the validity of the end result.

The presented methodology shows promising results in favor of a multi-technology and multi-sensors approach, since this integration contributes to increasing the signal to noise ratio. These multi-sensors allow determination of the quality of the sensors' contact, accounting for the validity of the measured parameters, as well as compensation and correction for the interferences (such as temperature).

While certain features of the invention have been illustrated and described herein, many modifications, substitutions, changes, and equivalents will now occur to those of ordinary skill in the art. The invention is described in detail with reference to a particular embodiment, but it should be understood that various other modifications can be effected and still be within the spirit and scope of the invention. It is, therefore, to be understood that the appended claims are intended to cover all such modifications and changes as fall within the true spirit of the invention.

We claim:

1. A device for non-invasively measuring glucose level in a subject comprising:
 a unitary external unit having a first portion and an opposing second portion configured to receive a part of the subject's body therebetween;
 (a) a first ultrasonic piezo element positioned on the first portion and a second ultrasonic piezo element positioned on the opposing second portion of said external unit, a first membrane covering the first ultrasonic piezo element and a second membrane covering the second ultrasonic piezo element for measuring glucose levels utilizing ultrasonics;
 (b) the first membrane and the second membrane constituting respective first and second capacitor plates with an auto-oscillating means connected thereto for measuring glucose levels utilizing electromagnetics; and
 (c) a heater and a thermal sensor both positioned on the first portion and spaced from the first ultrasonic piezo element for measuring glucose level by thermal characteristics.

2. The device according to claim 1, wherein said ultrasonic piezo elements, said capacitor plates and said heater and said thermal sensor are contained within said external unit.

3. The device according to claim 2, further comprising a main unit for controlling measurements, receiving glucose level values from said external unit and calculating a weighted combination of said glucose level values to produce an accurate glucose reading; and, means for electrically connecting said main unit and said external unit.

4. The device according to claim 3 wherein said ultrasonic piezo elements include a transducer and a receiver.

5. The device according to claim 2, wherein said external unit further comprises means for determining a distance between said first portion and said opposing second portion.

6. The device according to claim 5, wherein said means for determining comprises a magnet and a sensor.

7. The device according to claim 5, wherein said external unit further comprises an adjustment screw setting a distance between said first portion and said opposing second portion.

8. The device according to claim 2, wherein said external unit further includes an ambient temperature sensor.

* * * * *